United States Patent [19]

Martin

[11] Patent Number: 5,063,791
[45] Date of Patent: Nov. 12, 1991

[54] SAMPLING OF MATERIAL

[75] Inventor: William J. Martin, Greater Manchester, England

[73] Assignee: National Research Development Corporation, London, England

[21] Appl. No.: 326,549

[22] PCT Filed: Aug. 1, 1988

[86] PCT No.: PCT/GB88/00638

§ 371 Date: Mar. 13, 1989

§ 102(e) Date: Mar. 13, 1989

[87] PCT Pub. No.: WO89/01026

PCT Pub. Date: Feb. 9, 1989

[30] Foreign Application Priority Data

Jul. 31, 1987 [GB] United Kingdom ............... 8718232

[51] Int. Cl.$^5$ .................... C12M 1/32; G01N 1/12
[52] U.S. Cl. .................. 73/864.31; 73/864.72; 435/292
[58] Field of Search ......... 73/864.72, 864.31, 864.23, 73/864.24, 864.25; 422/63-67; 436/43, 45, 47, 48, 49; 435/287, 292, 293, 295, 312

[56] References Cited

U.S. PATENT DOCUMENTS

| 3,321,954 | 5/1967 | Bailey .................. 73/864.31 X |
| 3,490,289 | 1/1970 | Mangin ................. 73/864.31 |
| 3,776,184 | 12/1973 | Harrison ............... 73/864.72 X |
| 3,778,351 | 12/1973 | Rosov . | |
| 3,841,973 | 10/1974 | Wilkins et al. ......... 73/864.31 |
| 3,844,869 | 10/1974 | Sharpe . | |
| 4,198,483 | 4/1980 | Sogi et al. ............. 73/864.31 X |
| 4,204,431 | 5/1980 | Schulz ................. 73/864.31 |
| 4,242,909 | 1/1981 | Gundelfinger .......... 73/864.21 |
| 4,287,301 | 1/1981 | Astle .................. 435/292 X |
| 4,488,814 | 12/1984 | Johnson ............... 356/414 |
| 4,616,515 | 10/1986 | Dancoine .............. 73/864.31 |
| 4,742,715 | 5/1988 | Heinz et al. ........... 73/864.31 |
| 4,824,641 | 4/1989 | William ............... 73/864.12 X |

FOREIGN PATENT DOCUMENTS

| 2755568 | 5/1979 | Fed. Rep. of Germany ... 73/864.72 |
| 2527221 | 5/1983 | France . |
| 5323 | 9/1987 | PCT Int'l Appl. . |
| 7911 | 12/1987 | PCT Int'l Appl. . |
| 1100306 | 1/1968 | United Kingdom ............ 73/864.31 |
| 2122640 | 3/1986 | United Kingdom . |

OTHER PUBLICATIONS

International Search Report on Applicant's International Appln. No. PCT/GB88/00638; published with PCT WO89/01026 on Feb. 9, 1989.

Primary Examiner—Tom Noland
Attorney, Agent, or Firm—Cushman, Darby & Cushman

[57] ABSTRACT

Apparatus for sampling material, e.g. a microbiological growth culture, comprises a consumable sampling filament (3) which may be advanced through a tubular guide (1) so that a tip (3a) projects therefrom. The guide (1) and tip (3a) are moved relatively towards the material to be sampled, a portion of which is collected on the tip. After moving the guide and tip relatively away from the material, the filament (3) may be advanced through the guide and the tip severed by a cutter (9) so as to fall into a receiving vessel (8) containing, for example, a nutrient liquid.

22 Claims, 4 Drawing Sheets

SAMPLING OF MATERIAL

FIELD OF THE INVENTION

The present invention relates to the sampling of material, particularly but not exclusively microbiological material.

BACKGROUND OF THE INVENTION

Plating out and culture inoculation is a procedure used extensively in life science laboratories. For example, the technique finds wide application in clinical biology as a means of disease identification and treatment, in molecular biology as part of the Sanger DNA sequencing protocol and in pharmaceutical research to screen antibiotics. Briefly, the method comprises growing microbiological material in, for example, a Petri-dish and the selecting from the resultant growth (or lawn) those colonies or plaques (e.g. of yeasts, fungi, bacteria or virus infected plaques) which are required for further study or amplification. The technique is currently effected manually by experienced personnel who, identify the colonies or plaques of interest, then 'pick-out' these colonies or plaques with individual sampling probes (usually sterile pointed sticks). The colonies or plaques are then transferred individually to discrete culture tubes or containers in which they are incubated prior to further processing. Many laboratories require hundreds, and possibly thousands, of such operations to be effected daily in a process which is manpower intensive, tedious, repetitive and error prone. Additionally, many cultures of interest may be harmful and consequently there is a health risk with the transfer of such cultures. Furthermore, human operators carry a wide variety of organisms and it is, therefore, difficult to maintain sterile operating conditions when the procedure is being carried out manually.

DESCRIPTION OF THE RELATED ART

WO87/05323 and WO87/07911 each describe a method of sampling microbiological material by advancing an elongate strip of material between a sampling position and a transfer position. A portion of the strip is caused to contact the microbiological material at the sampling position and the strip is then advanced so that the sample is at the transfer position at which it is removed from the strip. Between the sampling and transfer positions, the strip will be carrying a number of samples and it is generally necessary to isolate them from each other to prevent contamination. Additionally, the strip and its containing cassette are mechanically quite complex. These represent disadvantages of these processes.

GB-B-2 122 640 describes an automatic bacterial colony transfer apparatus in one embodiment of which a metal wire stored on a reel thereof is used as a sampling element. The method disclosed comprises collecting a sample of the bacterial colony on a tip of the wire, and then accurately controllably moving the tip so as to contact it with a receiving surface (e.g. a growth medium to which a portion of the sample is transferred. The wire is then pulled off the reel by a feeder device, held by a clamp, and the tip severed (for disposal) to leave a fresh tip for sampling.

SUMMARY OF THE INVENTION

According to a first aspect of the present invention there is provided sampling apparatus comprising a guide element for location of the tip of an elongate sampling element and for guiding axial movement of said sampling element, means for effecting relative movement of the guide element and tip towards and away from a material to be sampled, holding means for holding the sampling element axially relative to the guide element, advancement means for advancing the sampling element axially relative to the guide element, and discharge means for discharging the tip away from the guide element complete with any sampled material.

According to a second aspect of the invention there is provided a method of obtaining a sample of material using the tip of an elongate sampling element which is located by a guide element from which the tip projects, the method comprising retaining the sampling element axially relative to the guide element, effecting relative movement of the material to be sampled towards the guide element and tip so that said tip contacts and samples the material, effecting the reverse of said relative movement, discharging the tip away from the guide element with or without transfer of the sample therefrom and advancing sampling element axially relative to the guide element.

Preferably the tip is discharged after the sampling element has been axially advanced relative to the guide element.

Most preferably, it is the guide which is moved towards and away from the material being sampled. In this case, the advancement means for advancing the filament relative to the guide should be capable of simultaneous vertical movement with the guide so that (during this movement) the sampling element is not moved relative to the guide.

The guide element serves to ensure that the short projecting length (i.e. the tip) of the sampling element is comparatively "rigid". Consequently, when the guide member and tip are moved together relatively towards the material to be sampled, the tip maintains the direction in which it points and thus may be used to contact a pre-determined location in the material being sampled. This is particularly important in the case of sampling a particular colony from a microbiological growth culture.

Preferably the guide is tubular and the sampling element is a close fit therein.

Various possible forms of sampling element may be used. Most preferably the sampling element is a filament (preferably of plastics material) drawn from a reel thereof. Alternatively, the sampling element may be tubular and a reduced pressure may be applied within the tubular sampling element to assist in collection of material at the tip thereof.

In a further alternative the elongate sampling element may be supplied in short lengths to the guide, e.g. by cutting at the inlet to the guide or by manufacturing as such. The short lengths may then be moved relative to the guide in a two stage action using a "chuck-type" mechanism, the first stage providing the projecting sampling tip and a second stage ejecting the whole length. In a modification the sampling element is supplied to the guide as an elongate length with spaced weaknesses, the arrangement being such that the sampling element is severed at the weak points as it is advanced through the guide.

In the case where the sampling element is supplied to the guide as a continuous length, the holding means and advancement means are preferably provided by a pair of rollers at least one of which is driven and between which the sampling element is gripped.

The discharge means preferably comprise severing means, e.g. opposed blades or a hot wire.

When the invention is applied to the sampling of microbiological material, the discharged tip of the filament may be dropped straight into a receiver (e.g. a culture tube or the like) containing a suitable nutrient liquid for growth of the microbiological material. If the filament is of plastics material it should not adversely effect the growth of the microbiological material. The method therefore avoids the need for a separate operation for transferring the microbiological material from the filament, as occurs in the 'strip' techniques described in the aforementioned applications. This assists in the maintenance of sterile conditions in the sampling process. Furthermore, the need for accurate positioning of the step for transfer of the material is avoided (since the tip may simply be dropped into a comparatively wide receiver) and all of the sample is transferred.

The method of the invention lends itself readily to automation and may be incorporated into a fully automatic sampling system. Such a system may comprise automatic visual recognition means for identifying colonies of interest and locating their position in a growth culture. Information from the visual recognition means is then used to control the positioning of the growth culture relative to the tip of the sampling element so that the colony or plaque of interest is proximate the tip. The guide member and sampling element may be incorporated in a mechanical handling robot which effects the sampling procedure. Using such a system a plurality of colonies from each of successive growth cultures supplied to the system may be rapidly sampled and transferred for culture inoculation or other processing.

The invention will now be further described by way of example and with reference to the accompanying drawings, in which:

DESCRIPTION OF THE PREFERRED EMBODIMENT

Figure 1A:
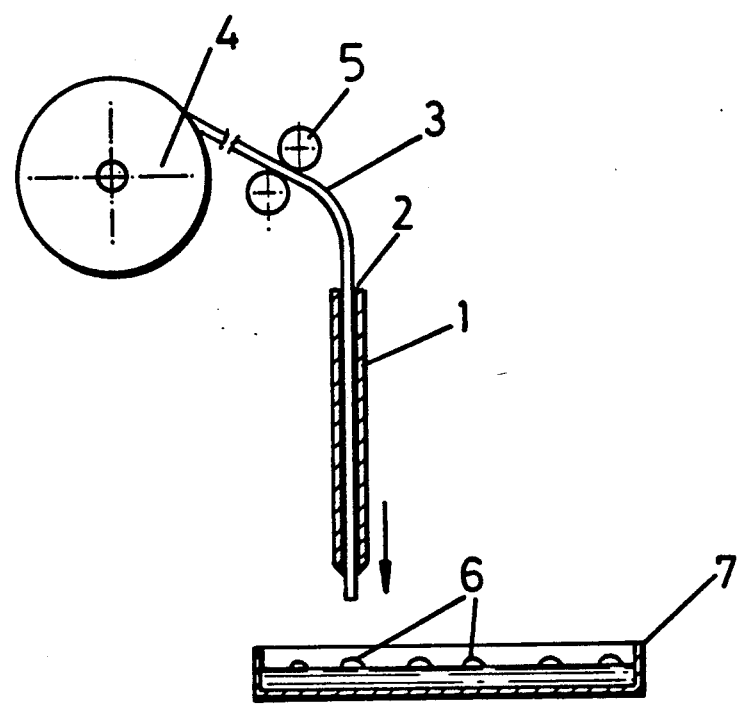
FIGS. 1a-1d are diagrammatic representations of illustrating stages in the method of the invention.

As shown in FIG. 1a, the apparatus comprises a vertically reciprocable rigid metal plunger 1 with a central bore 2 through which passes nylon monofilament 3 drawn from a reel 4 thereof. The monofilament is a close fit within the bore 2 and a tip 3a thereof projects from the guide 1. A friction drive arrangement 5 (e.g. a stepper motor) serves to advance and retract the filament 3 in the manner to be described below. Further, the friction drive arrangement 5 is capable of reciprocal vertical movement simultaneously with plunger 1.

Figure 1B:
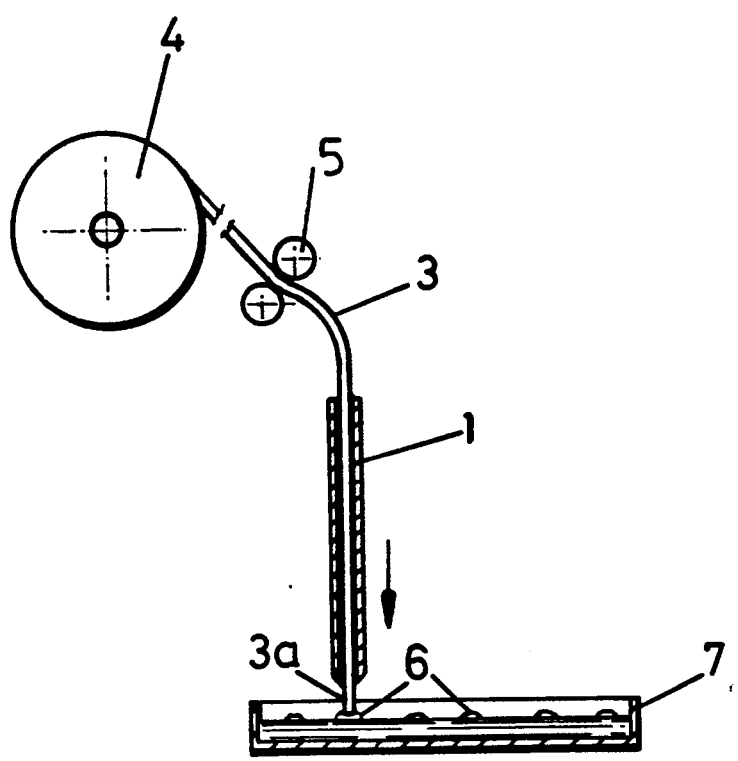
Figure 1C:
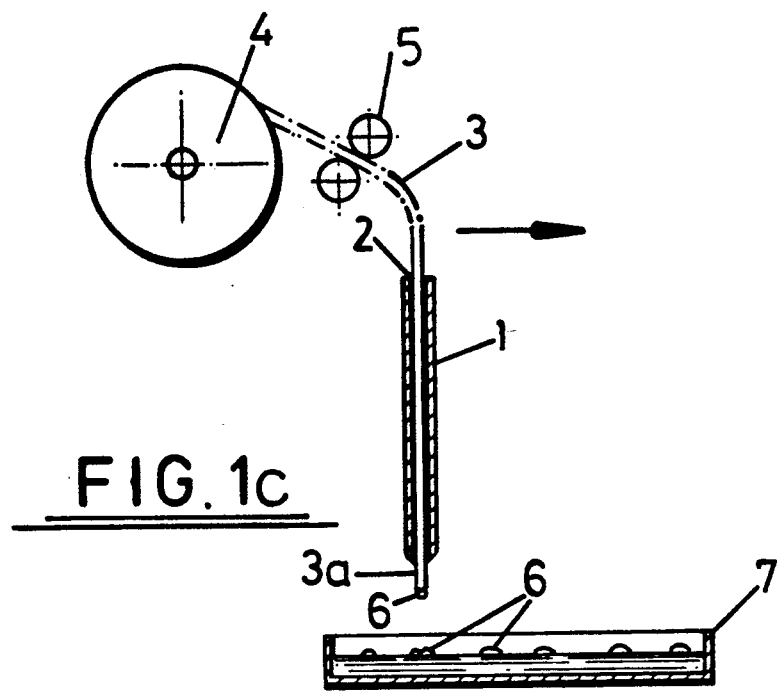
Figure 1D:
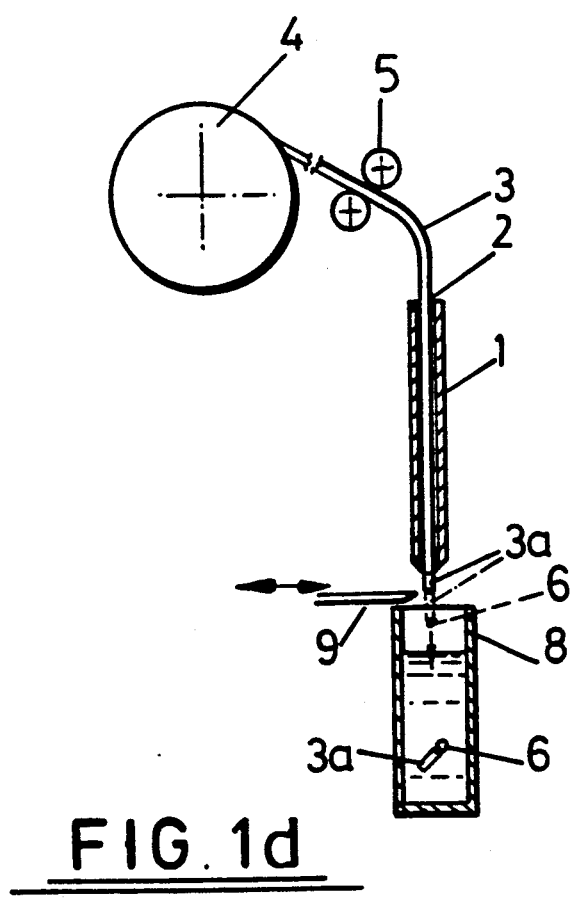
Figure 3:
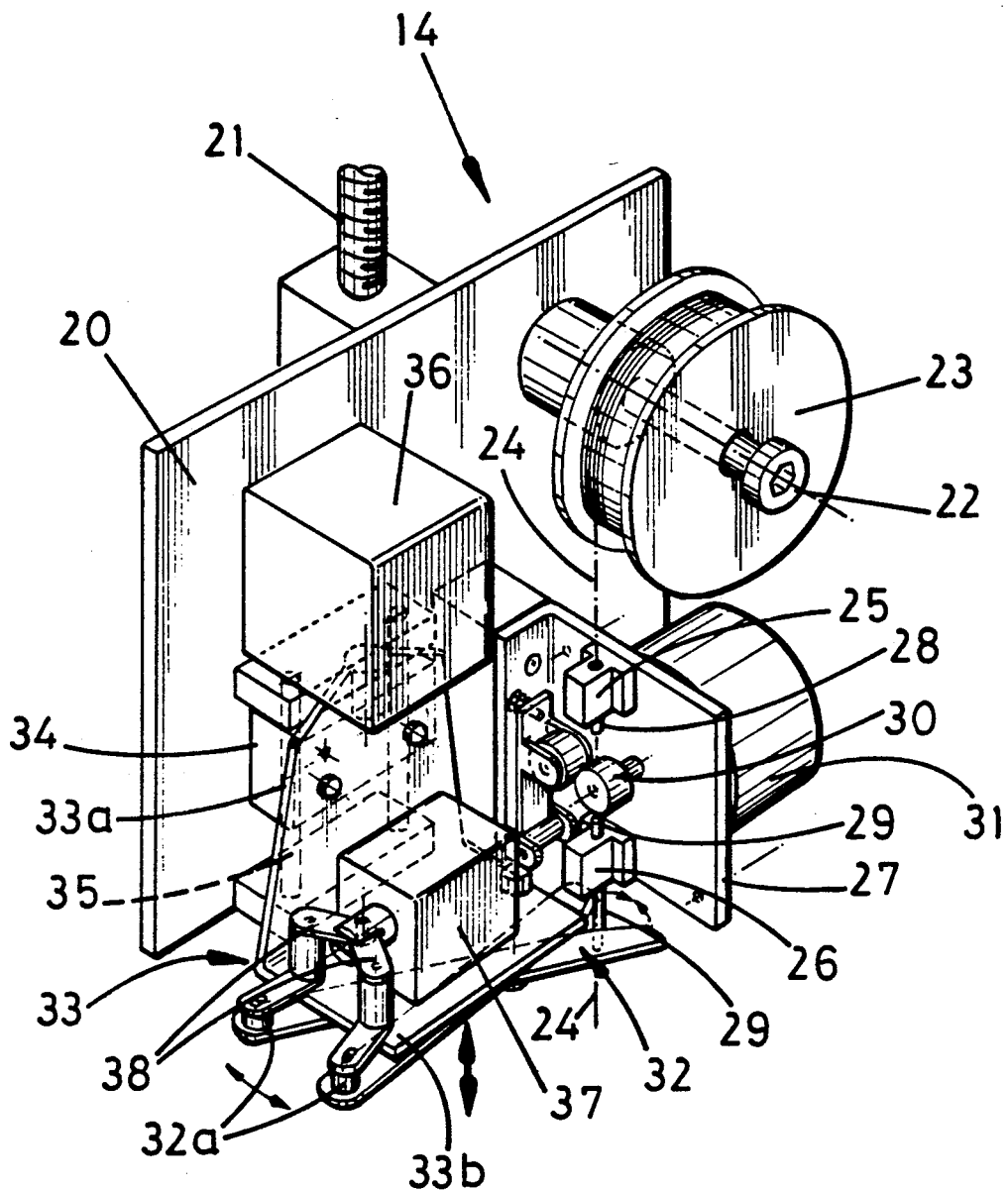
FIG. 3 shows a detail of FIG. 2.

FIG. 1a shows the apparatus in a position of readiness for sampling a colony 6 of microbiological material from a container 7. The tip 3a will be seen to be above the colony 6. In FIG. 1b guide 1 and friction drive 5 have been moved downwardly so that the tip 3a contacts and samples colony 6. This movement of the filament with the guide 1 ensures that the same length of tip 3a projects from guide 1 thereby maintaining the "rigidity" of the tip and therefore accurate sampling of the colony of interest. Subsequently, drive 5 and plunger 1 are moved upwardly so that the tip 3a is clear of container 7, as shown in FIG. 1c. Plunger 1 and drive 5 may now be moved relatively away from the container 7 to a position above a culture container 8 containing suitable nutrient liquid. Tip 3a is now extended (by operating drive arrangement 5) and is then severed by any suitable means, e.g. a blade 9, and drops into container 8, leaving the apparatus in the condition shown in FIG. 1d. Consequently, once plunger 1 is moved back above a further container 7, the above sequence may be repeated to effect a further sampling operation.

In a modification of the above described method of operation, the tip 3a is not dropped into container 8. The filament is extended so that the tip contacts the nutrient liquid (so that material is transferred thereto). Subsequently, the tip is moved clear of the nutrient liquid and then severed. In this case, the tip may then be disposed of.

Figures 2A, 2B:
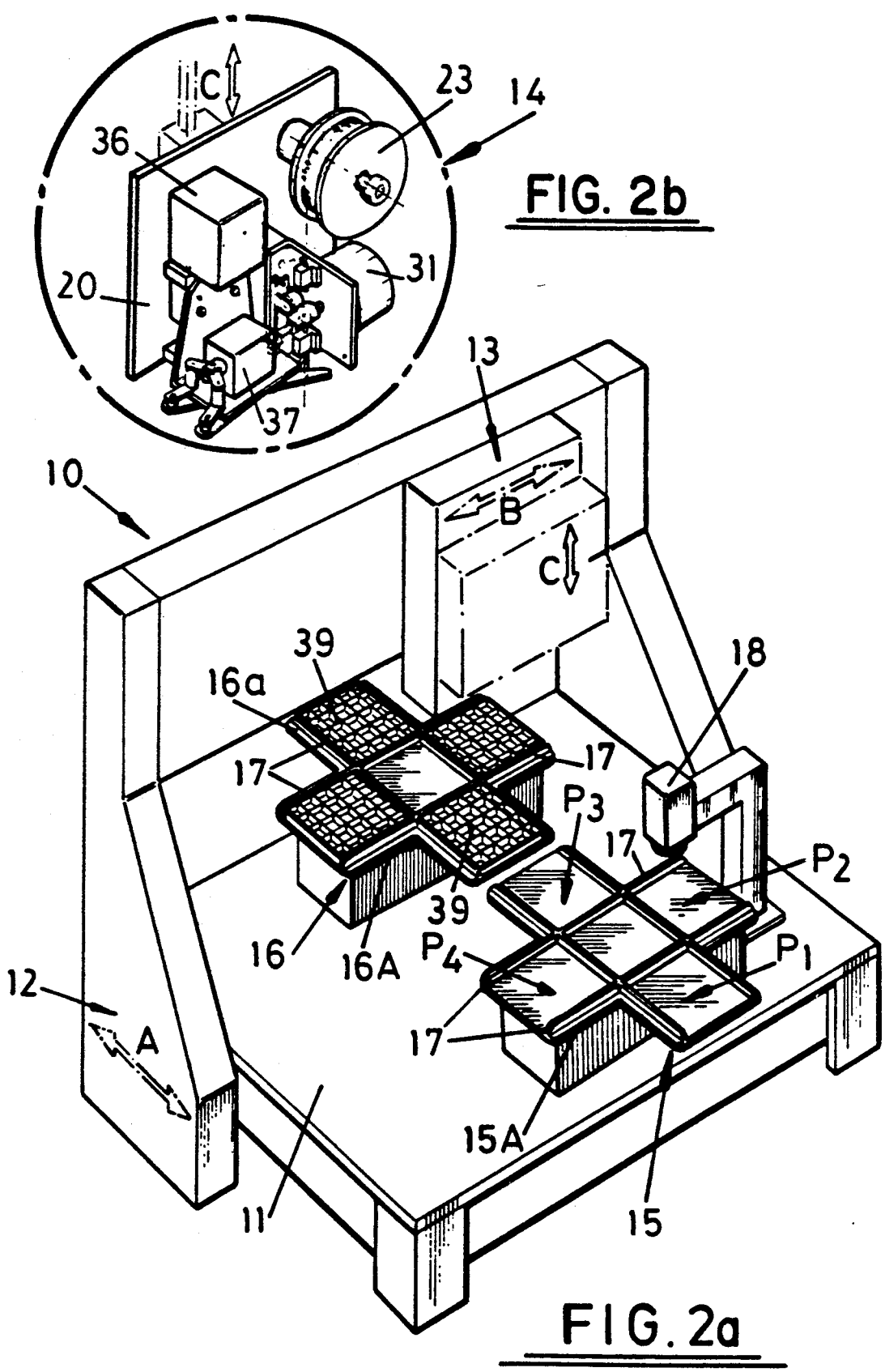
FIG. 2 is a perspective view of a sampling apparatus in accordance with the invention.

Referring now to FIG. 2 there is illustrated an apparatus 10 for automatic sampling using principles similar to those described with reference to FIGS. 1a to 1d.

The apparatus 10 comprises a platform 11 on which is mounted a gantry 12 for forward and rearward movement (arrows A). Supported on the gantry 12 is a carriage 13 for movement in either direction along gantry 12 (arrows B), and a sampling unit 14 is mounted on the carriage 13 such as to be movable upwardly and downwardly (arrows C) to effect sampling in the manner described in more detail below.

The movement of gantry 12 and carriage 13 may be effected by respective lead screw arrangements (not shown).

Front and rear carousels 15 and 16 respectively are provided on platform 11. Each such carousel is generally cruciform having four arms 15a or 16a (as the case may be) onto the free ends of which petri-dishes or similar containers may be slid by suitable handling apparatus. Each arm 15a or 16a has three low walls 17 positioned to allow the petri-dish or similar to be slid thereon and located in position.

The carousels 15 and 16 are each associated with respective rotary drive arrangements by means of which they may be indexed round to bring the arms 15a or 16a to various selected positions, as will be understood from the description given below.

Also provided is an imaging camera 18 positioned above platform 11 such that the arms 15a move beneath the camera lens upon rotation of the carousel 15. The camera 18 is intended to view microbiological cultures in petri-dishes (or the like) on arm 15a and supply images to computing means with pattern recognition software so that colonies of interest in the culture may be identified for subsequent sampling.

The sampling unit 14 will now be described in more detail. All components of this unit are supported directly or indirectly on a plate 20 at the rear of which is a nut engaged by a lead screw 21 for upwards and downwards movement of unit 14.

The plate 20 has a spindle 22 on which is freely rotatably supported a reel 23 of plastics filament 24 (e.g. nylon monofilament) such that filament drawn from reel 23 may pass through vertically aligned bores in vertically spaced blocks 25 and 26 provided on a support plate 27. Fixed within the bore of upper block 25 and projecting downwardly by a short distance therefrom is a metal tube 28 with an inner diameter substantially equal to the outer diameter of the plastics filament 24. A length of similar metal tube 29 (coaxial with tube 28) is fixed in the bore of lower block 26. This tube 29 projects both upwardly and downwardly from block 26 such that its upper end terminates a short distance below the lower end of tube 28 and its lower end is below the bottom edge of plate 20. As shown in the drawing, the filament 24 passes through both of tubes 28 and 29.

Between the adjacent ends of tubes 28 and 29 are a pair of drive rollers 30 (e.g. with a rubber peripheral drive surface) between which the filament 24 is firmly gripped. One of rollers 30 is driven by a stepping motor 31 provided on the opposite side of support plate 27 to the rollers 30, the non-driven roller being biased against the driven roller A pair of pivotally openable and closable (i.e. scissor-like) filament cutters 32 are mounted on a vertically movable L-shaped carrier 33 having one plate-like vertical limb 33a and a horizontal plate-like limb 33b on the undersurface of which the cutters 32 are located. On the rear face of limb 33a is a block 34 having vertical apertures through which locate pillars 35 fixed relative to plate 20. Thus, pillars 35 serve to guide carrier 33 during its vertical movement between upper and lower limit positions. Such vertical movement is effected by means of a solenoid 36 mounted on plate 20 above carrier 33, the output of the solenoid being connected to the top of limb 33a of the carrier.

As mentioned, cutters 32 are mounted on the underside of limb 33b and are so positioned that at the upper limit of movement of carrier 33 the cutters 32 will be open with their two cutting edges (which project beyond limb 33b) locating just below block 26 to either side of tube 29. At the lower limit position of carrier 33 the cutting edges are located just below the lower end of tube 29.

As seen in the drawing, the overall length of cutters 32 is greater than that of limb 33b (of carrier 33) such that their non-cutting ends 32a project beyond that edge of limb 33b remote from the cutting edges. A solenoid 37 is mounted on the top of limb 33b and its output is connected to a pair of pivotal links 38 each of which is pivotally attached to an end 32a of the cutters 32.

Operation of solenoid 37 serves to operate the pivotal links 38 to open or close the cutters (as the case may be).

The illustrated apparatus is associated with computing means which serve to control movement of gantry 12, carriage 13, sampling unit 14, rotation of carousels 15 and 16 together with operation of stepper motor 31 and solenoids 36 and 37, and processing of information from camera 18 to provide for operation of the apparatus in accordance with the following description.

The arms of carousel 15 may be at any one of four positions, designated in the drawing as P1-4.

In operation of the apparatus, a petri-dish or the like containing colonies of material to be sampled is positioned on the arm 15a of carousel 15 at position P1. This may be done by automatic handling apparatus. Carousel 15 is then indexed around so that the petri-dish is at P2 beneath camera 18. This camera views the petri-dish and images from the camera are processed by the intelligent pattern recognition software so as to determine the positions of colonies of interest (which are to be sampled) in the culture.

Carousel 15 is now indexed around so that the petri-dish is at P3 where sampling takes place.

The computer now controls movement of gantry 12 and carriage 13 so that the tip of filament 24 is above the colony of interest. It should be noted that, during this movement, sampling unit 14 is at its upper position, as is the carrier 33, and that the cutters 32 are open.

Sampling unit 14 is now moved downwardly by rotation of lead screw 21 such that the tip of filament 24 contacts and samples a colony of interest. Lead screw 21 is then rotated in the opposite direction so as to raise unit 14. Gantry 12 and carriage 13 are now moved as necessary so that the tip of filament 24 (with sampled colony), is above a predetermined compartment in a compartmentalised sampling tray 39 on carousel 16. Simultaneously with this movement, stepper motor 31 is operated to advance filament 24 a further distance beyond the lower end of tube 29. Once the tip of filament 24 is above the predetermined compartment, solenoid 36 is operated to move carrier 33 to its lower limit position (at which the cutting edges of the cutters 32 are below tube 29) and solenoid 37 is actuated such the cutters snip the tip of filament 24, allowing it to fall into the compartment.

Gantry 12 and carriage 13 are now moved such that the tip of filament 24 is again above a colony to be sampled in the petri-dish at P3. During the movement, stepper motor 31 is operated to withdraw filament back through tube 29 so that only a short tip projects therefrom in readiness for the next sampling operation.

Once sufficient samples have been collected in tray 39, carousel 16 may be indexed round to bring a fresh tray to P1. The tray 39 containing the sample may subsequently be discharged from carousel 16 and a fresh tray loaded in its place.

I claim:

1. Sampling apparatus comprising a guide element for location of the tip of an elongate sampling element and for guiding axial movement of said sampling element, means for effecting relative movement of the guide element and tip towards and away from a material to be sampled, holding means for holding the sampling element axially relative to the guide element, advancement means for advancing the sampling element axially relative to the guide element, means for moving the sampling element and tip with any sampled material thereon to a sample discharge station having thereat sample-receiving medium and discharge means at the station for discharging the tip away from the sampling element complete with any sampled material on the tip into the medium.

2. Apparatus according to claim 1 wherein the discharge means comprises severing means for severing the tip of the sampling element.

3. Apparatus according to claim 1 wherein the guide element and the advancement means are mounted on a common vertically movable support member so as to be simultaneously vertically movable.

4. Apparatus as claimed in claim 3 wherein said discharge means is mounted on a carrier on the vertically moveable support member and the carrier is vertically movable relative to said support member.

5. Apparatus as claimed in claim 4 wherein the discharge means comprises severing means pivotally openable and closable by means of a first solenoid and the vertical movement of the severing means relative to the support member is effected by means of a second solenoid.

6. Apparatus as claimed in claim 3 wherein the vertically movable support member is mounted on a carriage movable along a gantry, said support member, carriage and gantry being movable in three mutually perpendicular directions.

7. Apparatus as claimed in claim 1 wherein the advancement means and the holding means are provided by a pair of rollers at least one of which is driven and between which the sampling element is gripped.

8. Apparatus as claimed in claim 1 wherein the guide element is tubular.

9. Apparatus as claimed in claim 1 for use with a tubular sampling element wherein means are provided for applying a reduced pressure to the interior of the tubular sampling element so as to assist collection of material at the tip.

10. Apparatus as claimed in claim 1 provided with the sampling element.

11. Apparatus as claimed in claim 10 wherein the sampling element is a filament.

12. Apparatus as claimed in claim 10 wherein the sampling element is tubular.

13. Apparatus as claimed in claim 10 wherein the sampling element is of plastics material.

14. A method of obtaining a sample of material using the tip of an elongate sampling element which is located by a guide element from which the tip projects, the method comprising retaining the sampling element axially relative to the guide element, effecting relative movement of the material to be sampled towards the guide element and tip so that said tip contacts and samples the material, effecting the reverse of said relative movement, effecting relative movement between a sampling station having a medium thereat and the guide element and tip with the sample thereon to position the tip for discharge into the medium, discharging the tip away from the sampling element directly into the medium and advancing the sampling element axially relative to the guide element.

15. A method as claimed in claim 14 wherein the tip is discharged from the guide element by severing of the sampling element.

16. A method as claimed in claim 15 wherein said advancement of the sampling element is effected prior to severing thereof.

17. A method as claimed in claim 15 wherein the severed tip with sampled material thereon is discharged into a receiver for further treatment of the sampled material on the tip.

18. A method as claimed in claim 14 wherein the receiver contains nutrient medium.

19. A method as claimed in claim 14 wherein the guide element is tubular and the sampling element is a close fit therein.

20. A method as claimed in claim 14 wherein the sampling element is a plastics filament.

21. A method as claimed in claim 14 wherein the sampling element is tubular and reduced pressure is applied therein to assist in collection of the sample at the tip.

22. A method as claimed in claim 14 wherein the material to be sampled are colonies or plaques of a microbiological growth culture.

* * * * *